(12) United States Patent
Okaguchi et al.

(10) Patent No.: US 7,803,632 B2
(45) Date of Patent: Sep. 28, 2010

(54) METHOD FOR DETECTING SUBSTANCE IN LIQUID AND SENSOR FOR DETECTING SUBSTANCE IN LIQUID

(75) Inventors: Kenjiro Okaguchi, Moriyama (JP); Michio Kadota, Kyoto (JP)

(73) Assignee: Murata Manufacturing Co., Ltd, Kyoto (JP)

( * ) Notice: Subject to any disclaimer, the term of this patent is extended or adjusted under 35 U.S.C. 154(b) by 0 days.

(21) Appl. No.: 12/273,571

(22) Filed: Nov. 19, 2008

(65) Prior Publication Data
US 2009/0061529 A1    Mar. 5, 2009

Related U.S. Application Data

(63) Continuation of application No. PCT/JP2007/059086, filed on Apr. 26, 2007.

(30) Foreign Application Priority Data
Jun. 8, 2006    (JP) ............... 2006-159946

(51) Int. Cl.
*G01N 25/08*    (2006.01)
(52) U.S. Cl. ............. 436/150; 73/335.02; 73/335.03; 73/335.04; 73/335.05; 73/335.06; 422/68.1; 422/82.01; 422/82.02; 436/149; 436/151
(58) Field of Classification Search .......... 422/68.1, 422/82.01–82.04; 436/149–151; 338/27, 338/28, 34; 73/335.02–335.06
See application file for complete search history.

(56) References Cited

U.S. PATENT DOCUMENTS 4,862,110 A    8/1989    Charbonnier (Continued)

FOREIGN PATENT DOCUMENTS

JP    09-189685 A    7/1997

(Continued)

OTHER PUBLICATIONS

Harding et al., Love wave acoustic immunosensor operating in liquid, 1997, Elsevier Science, Sensors and Actuators A 61, p. 279-286.*

(Continued)

*Primary Examiner*—Tony G Soohoo
*Assistant Examiner*—Robert Eom
(74) *Attorney, Agent, or Firm*—Keating & Bennett, LLP (57) ABSTRACT

A method for detecting a substance in a liquid with high accuracy and high sensitivity includes recording frequency drifts of output frequencies of oscillator circuit outputs of m sensing oscillator circuits respectively including sensing SAW elements and frequency drifts of output frequencies of oscillator circuit outputs of n reference oscillator circuits respectively including reference SAW elements; determining at least one of the sensing oscillator circuits whose frequency drifts fall within a predetermined range and at least one of the reference oscillator circuits whose frequency drifts fall within the predetermined range to be acceptable; selecting at least one of the sensing oscillator circuits from among the acceptable sensing oscillator circuits and at least one of the reference oscillator circuits from among the acceptable reference oscillator circuits; and comparing an oscillator circuit output of the selected at least one of sensing oscillator circuits with an oscillator circuit output of the selected at least one of reference oscillator circuits to thereby detect a detection target substance.

8 Claims, 5 Drawing Sheets

U.S. PATENT DOCUMENTS

| | | | |
|---|---|---|---|
| 5,138,869 | A | 8/1992 | Tom |
| 5,411,709 | A | 5/1995 | Furuki et al. |
| 5,817,922 | A * | 10/1998 | Rapp et al. .................. 73/24.06 |
| 6,890,715 | B1 * | 5/2005 | Lewis et al. .................... 435/6 |
| 6,895,338 | B2 * | 5/2005 | Hsiung et al. ................. 702/22 |
| 7,389,673 | B2 | 6/2008 | Kimura et al. |

FOREIGN PATENT DOCUMENTS

| | | |
|---|---|---|
| JP | 2000-31741 A | 1/2001 |
| JP | 3481298 B2 | 12/2003 |
| JP | 3488554 B2 | 1/2004 |
| JP | 2006-47229 A | 2/2006 |
| WO | 2006/027893 A1 | 3/2006 |
| WO | 2006/027945 A1 | 3/2006 |

OTHER PUBLICATIONS

Shiokawa et al.: "Surface Acoustic Wave Sensor for Liquid-Phase Application," 1999 IEEE Ultrasonics Symposium; 1999; vol. 1; pp. 445-452.

Cunningham et al.: "Design, Fabrication and Vapor Characterization of a Microfabricated Flexural Plate Resonator Sensor and Application to Integrated Sensor Arrays," Sensors and Actuators; 2001; pp. 112-123.

Fadel et al.: "Coupled Determination of Gravimetric and Elastic Effects on Two Resonant Chemical Sensors: Love Wave and Microcantilever Platforms," 2003 IEEE International Frequency Control Symposium and PDA Exhibition Jointly with the 17th European Frequency and Time Forum; 2003; pp. 964-970.

Bender et al.: "Development of a Preconcentration Unit for a Saw Sensor Micro Array and Its Use for Indoor Air Quality Monitoring," Sensors and Actuators; 2003; pp. 135-141.

Kim et al.: "Development of Biosensor Using Surface Acousitc Wave," The 30th Annual Conference of the IEEE Industrial Electronics Society; Nov. 2-6, 2004; pp. 1546-1549.

Kondoh et al.: "Identification of Liquid Samples Using SH-Saw Sensors," The Transactions of the Institute of Electronics Information and Communication Engineers; 1995; vol. J78, No. 1; pp. 54-61.

Official Communication issued in International Patent Application No. PCT/JP2007/059086, mailed on Jun. 12, 2007.

Okaguchi et al.; "Sensor for Detecting Substance in Liquid"; U.S. Appl. No. 12/273,657, filed Nov. 19, 2008.

Okaguchi et al.; "Sensor for Detecting Substance in Liquid"; U.S. Appl. No. 12/273,569, filed Nov. 19, 2008.

* cited by examiner

METHOD FOR DETECTING SUBSTANCE IN LIQUID AND SENSOR FOR DETECTING SUBSTANCE IN LIQUID

BACKGROUND OF THE INVENTION

1. Field of the Invention

The present invention relates to a method for detecting a substance in a liquid using a surface acoustic wave element (SAW element) and a sensor for detecting a substance in a liquid and, more particularly, to a method for detecting a substance in a liquid that uses a sensor for detecting a substance in a liquid provided including a plurality of sensing SAW elements and a plurality of reference SAW elements, and the sensor for detecting a substance in a liquid.

2. Description of the Related Art

In the related art, in order to detect an antigen, an antibody, a protein, or other substance in a liquid, a sensor for detecting the substance in the liquid that includes a surface acoustic wave element (SAW element) is used. WO2006/027893A1 describes an example of a sensor for detecting a substance in a liquid of this type.

Figure 6A:
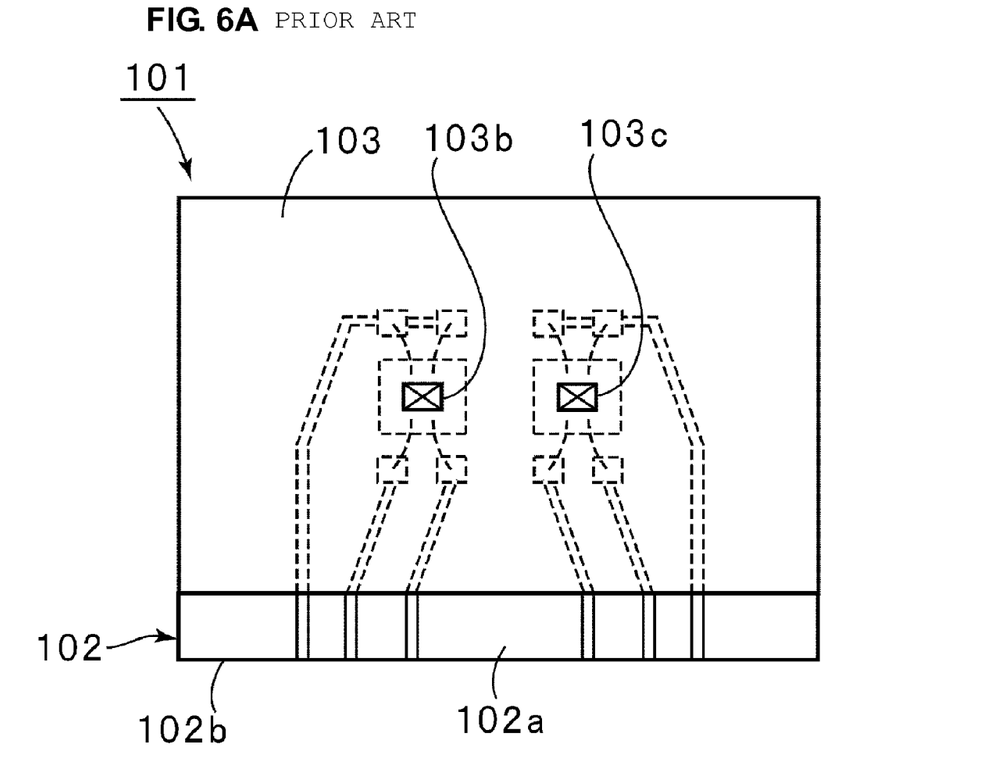
FIG. 6A is a schematic plan view that shows an example of a known sensor for detecting substance in a liquid.
Figure 6B:
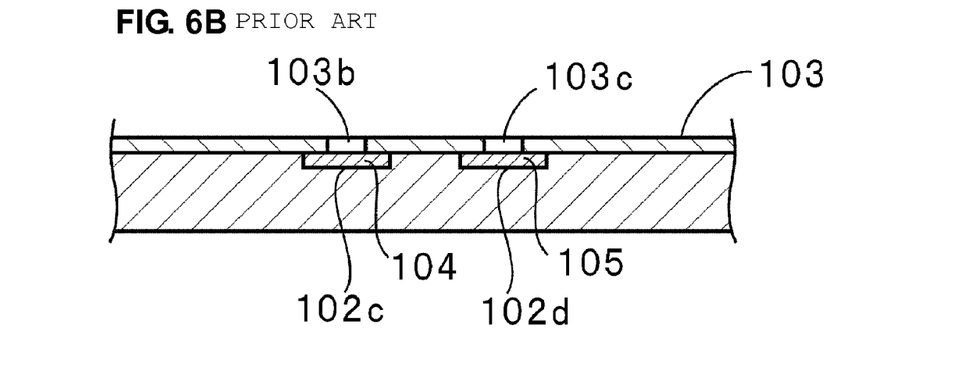
FIG. 6B is a cross-sectional view that shows a major portion thereof.

FIG. 6A is a plan view that illustrates a sensor for detecting a substance in a liquid described in WO2006/027893A1. FIG. 6B is a front cross-sectional view that shows the major portion thereof.

The sensor for detecting a substance in a liquid 101 includes a base substrate 102. Recesses 102c and 102d are provided on the upper surface 102a of the base substrate 102. A sensing SAW element 104 and a reference SAW element 105 are respectively provided in the recesses 102c and 102d. A resin layer 103 is laminated on the base substrate 102 so as to be arranged at a distance from one end 102b. The resin layer 103 includes through-holes 103b and 103c that face the recesses 102c and 102d, respectively. The sensing SAW element 104 includes a piezoelectric substrate, an IDT electrode provided on the piezoelectric substrate, and a reaction film arranged so as to cover the IDT electrode. The reaction film is made of a material that reacts with a detection target substance, as a sample, in a liquid to bond with the detection target substance. The reference SAW element 105 includes an IDT electrode provided on a piezoelectric substrate. No reaction film is provided for the reference SAW element 105.

In use, at least portions including the through-holes 103b and 103c are submerged in a liquid, and in the sensing SAW element 104, the reaction film reacts with the detection target substance to bond with the detection target substance. Thus, in the sensing SAW element 104, a mass applied to a portion at which the IDT electrode is provided increases due to the bonding of the detection target substance. In contrast, in the reference SAW element 105, no reaction film that reacts with the detection target substance is provided, so that an increase in additive mass due to bonding of the detection target substance does not occur.

In the sensor for detecting substance in a liquid 101 described in WO2006/027893A1, a variation in acoustic velocity of a surface acoustic wave due to the additive mass in the sensing SAW element 104 is detected as a variation in electrical signal. In this case, by obtaining a difference between an output from the sensing SAW element and an output from the reference SAW element 105, it is possible detect the detection target substance.

In addition, WO2006/027945A1 describes a similar sensor for detecting substance in a liquid.

In the sensor for detecting substance in a liquid 101 described in WO2006/027893A1, if no detection target substance, such as a protein, that reacts with the reaction film is present, the sensing SAW element and the reference SAW element must have substantially the same behavior, that is, substantially the same frequency characteristic. However, among SAW elements, some have large variations in frequency variation when a liquid is attached thereto. When such SAW devices are used as the sensing SAW element or the reference SAW element, the detection sensitivity of a protein, or other substance, decreases and, in some cases, an erroneous detection result may occur.

That is, it may be determined that a detection target substance is present when no detection target substance is actually present, or it may be determined that no detection target substance is present when a detection target substance is actually present.

SUMMARY OF THE INVENTION

To overcome the problems described above, preferred embodiments of the present invention provide a method for detecting substance in a liquid that uses a sensor for detecting a substance in a liquid having a sensing SAW element and a reference SAW element that is capable of accurately and reliably detecting a detection target substance in a liquid, and provide a sensor for detecting a substance in a liquid.

According to a preferred embodiment of the present invention, a method for detecting substance in a liquid that uses a sensor for detecting a substance in a liquid that includes a sensing oscillator circuit including a sensing SAW element with a sensing portion having an IDT and a reaction film that is arranged so as to cover the IDT and that reacts with a substance in a liquid, and a first amplifier element connected to the sensing SAW element; a reference oscillator circuit that includes a reference SAW element having an IDT but no reaction film that covers the IDT, and a second amplifier element connected to the reference SAW element; and a recording unit arranged to record an oscillator circuit output of the sensing oscillator circuit and an oscillator circuit output of the reference oscillator circuit, includes: providing a number m of the sensing oscillator circuits, where m is an integer greater than or equal to 2 and a number n of the reference oscillator circuits, where n is an integer greater than or equal to 2; a first step of recording output frequencies fs1 to fsm of the m sensing oscillator circuits and output frequencies of the n reference oscillator circuits; a second step of measuring a frequency drift of each of the output frequencies of the m sensing oscillator circuits and each of the output frequencies of the n reference oscillator circuits; a third step of determining that, when the frequency drift measured in the second step falls within a predetermined range, the corresponding sensing oscillator circuit or the corresponding reference oscillator circuit is accepted and, when the frequency drift falls outside the predetermined range, the corresponding sensing oscillator circuit or the corresponding reference oscillator circuit is rejected; a fourth step of selecting at least one of the sensing oscillator circuits, having a characteristic in the vicinity of a desired characteristic, from among the sensing oscillator circuits determined to be accepted in the third step and at least one of the reference oscillator circuits, having a characteristic in the vicinity of a desired characteristic, from among the reference oscillator circuits determined to be accepted in the third step; and a fifth step of bringing a liquid that includes a detection target substance into contact with the sensor for detecting a substance in a liquid and comparing an output frequency of the at least one of the sensing oscillator circuits selected in the fourth step with an output frequency of the at least one of the reference oscillator circuits selected in the fourth step to thereby detect the detection target substance.

More preferably, the rejected sensing oscillator circuits and the rejected reference oscillator circuits are not used in the following steps after they are determined to be rejected in the third step. Thus, in the following steps, the rejected sensing oscillator circuits and the rejected reference oscillator circuits are not used. Thus, it is possible to effectively reduce the time required for the following steps and reduce costs.

More preferably, in the third step, the predetermined range of the frequency drift is in the range of about −10 ppm/minute to about 0 ppm/minute. In this case, because the predetermined range is specifically set in this range, it is possible to further easily determine the sensing oscillator circuits and reference oscillator circuits that are not used.

In the method for detecting substance in a liquid according to this preferred embodiment of the present invention, more preferably, in the third step, at least one of the sensing oscillator circuits is selected in the order from the sensing oscillator circuit having a smaller frequency drift and at least one of the reference oscillator circuits is selected in the order from the reference oscillator circuit having a smaller frequency drift. In this case, it is possible to more quickly determine the sensing oscillator circuits and reference oscillator circuits that are determined to be accepted and used for measurement.

Preferably, in the fifth step, the detection target substance is detected using the average of the output frequencies of the reference oscillator circuits, the average of the output frequencies of the sensing oscillator circuits, and variations in outputs of the sensing oscillator circuits due to the detection target substance. That is, the average of the output frequencies of the reference oscillator circuits and the average of the output frequencies of the sensing oscillator circuits are used, and based on these averages and variations in outputs of the sensing oscillator circuits due to a detection target substance; the detection target substance is accurately and reliably detected.

More preferably, through the third step and the fourth step, one sensing oscillator circuit having a minimum frequency drift is selected from among the m sensing oscillator circuits and one reference oscillator circuit having a minimum frequency drift is selected from among the n reference oscillator circuits. In this case, because one sensing oscillator circuit having a minimum frequency drift and one reference oscillator circuit having a minimum frequency drift are used, it is possible to more accurately detect a substance in a liquid.

Preferably, the method for detecting a substance in a liquid according to preferred embodiments of the present invention further includes, between the fourth step and the fifth step, a sixth step of, where an output frequency of the selected at least one of the sensing oscillator circuits is a sensing frequency and an output frequency of the selected at least one of the reference oscillator circuits is a reference frequency, calculating a frequency difference; and a seventh step of determining that, when the frequency difference falls within a predetermined range, a sensing sensitivity is acceptable and, when the frequency difference falls outside the predetermined range, the sensing sensitivity is unacceptable. In this case, in the sixth step, the frequency difference is calculated, and in the seventh step, it is determined based on the frequency difference whether the sensing sensitivity is acceptable or unacceptable. Thus, it is possible to more accurately detect a substance in a liquid.

Preferably, in the seventh step, when the predetermined range of the frequency difference fd is about −5 (ppm/minute) <fd<about 5 (ppm/minute), it is possible to more accurately determine whether sensing sensitivity is favorable or poor.

According to another preferred embodiments of the invention, a sensor for detecting a substance in a liquid includes a plurality of sensing oscillator circuits, each of which includes a sensing SAW element including a sensing portion having an IDT and a reaction film that is arranged so as to cover the IDT and that reacts with a detection target substance in a liquid, and a first amplifier element connected to the sensing SAW element; a plurality of reference oscillator circuits, each of which includes a reference SAW element having no reaction film provided on an IDT, and a second amplifier element connected to the reference SAW element; a recording unit that records output frequencies of the sensing oscillator circuits and output frequencies of the reference oscillator circuits; and a controller that determines whether a frequency drift of each of the output frequencies of the plurality of reference oscillator circuits and each of the output frequencies of the plurality of sensing oscillator circuits, which are recorded in the recording unit, falls within a predetermined range, and that detects the detection target substance in a liquid based on output frequencies from the sensing oscillator circuits and the reference oscillator circuits, which are determined to fall within the predetermined range. Thus, it is possible to accurately and reliably detect a detection target substance in a liquid.

In the method for detecting a substance in a liquid according to preferred embodiments of the present invention, in the first to third steps, from among the output frequencies of the m sensing oscillator circuits and the output frequencies of the n reference oscillator circuits, the sensing oscillator circuits and reference oscillator circuits whose frequency drifts fall within a predetermined range are determined to be allowed. Then, in the fourth step and the fifth step, based on outputs of the sensing oscillator circuits and reference oscillator circuits, which are determined to be allowed, that is, whose frequency drifts are relatively small, a detection target substance in a liquid is detected. Thus, it is possible to reliably detect a detection target substance in a liquid with high sensitivity.

Other features, elements, steps, characteristics and advantages of the present invention will become more apparent from the following detailed description of preferred embodiments of the present invention with reference to the attached drawings.

DETAILED DESCRIPTION OF THE PREFERRED EMBODIMENTS

Hereinafter, specific preferred embodiments of the present invention will be described with reference to the accompanying drawings.

Figure 1:
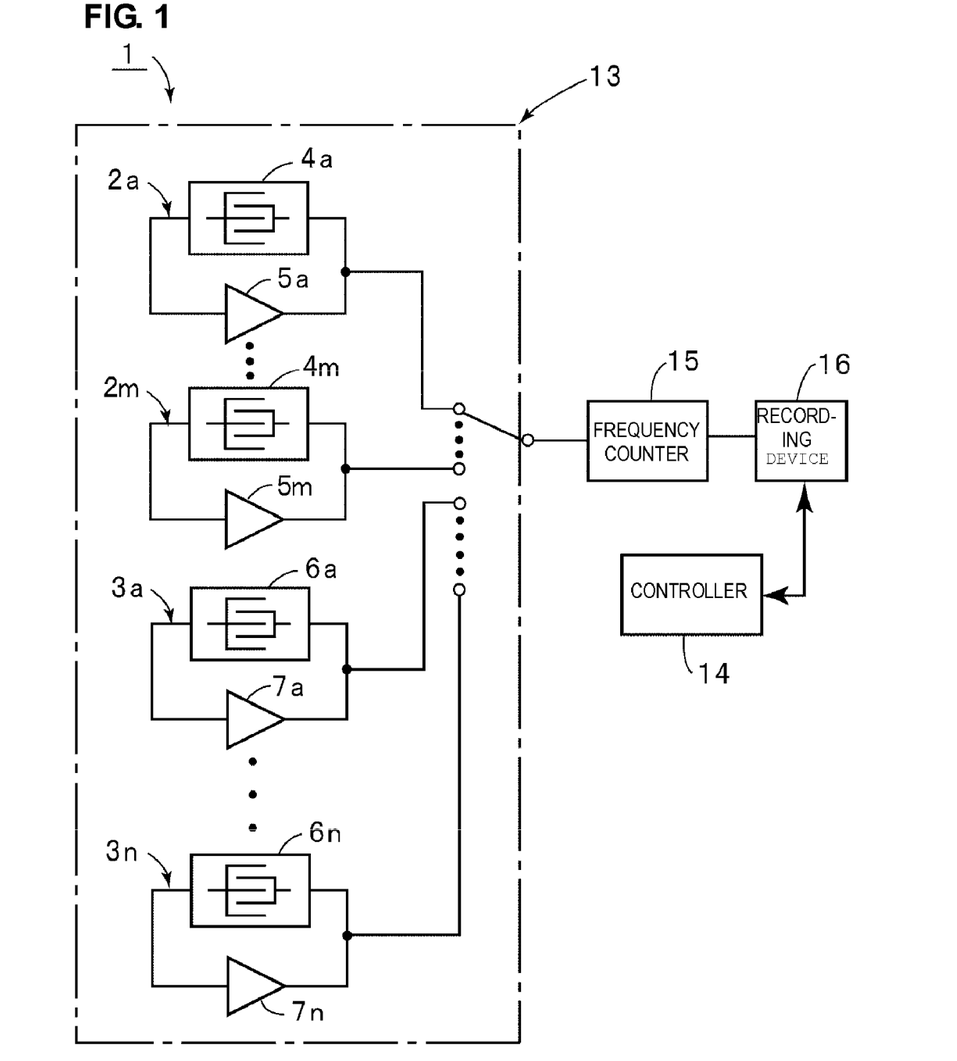
FIG. 1 is a block diagram that illustrates a sensor for detecting a substance in a liquid according to a preferred embodiment of the present invention.

FIG. 1 is a block diagram that illustrates the circuit configuration of a sensor for detecting a substance in a liquid according to a preferred embodiment of the present invention. The sensor for detecting a substance in a liquid 1 includes m sensing oscillator circuits 2a to 2m and n reference oscillator circuits 3a to 3n.

The sensing oscillator circuit 2a will be described as an example of the sensing oscillator circuits 2a to 2m. The sensing oscillator circuit 2a includes a sensing SAW element 4a and a first amplifier element 5a connected to the sensing SAW element 4a. The sensing SAW element 4a and the first amplifier element 5a define one oscillator circuit as shown in FIG. 1. The other sensing SAW elements 2b to 2m are also connected to corresponding first amplifier elements to define oscillator circuits. Thus, in the present preferred embodiment, the m sensing oscillator circuits 2a to 2m are provided.

On the other hand, in the reference oscillator circuit 3a, a second amplifier element 7a is connected to a reference SAW element 6a to define an oscillator circuit. The other reference oscillator circuits 3b to 3n are defined in a similar manner. Thus, the n reference oscillator circuits 3a to 3n are provided.

Figure 2:
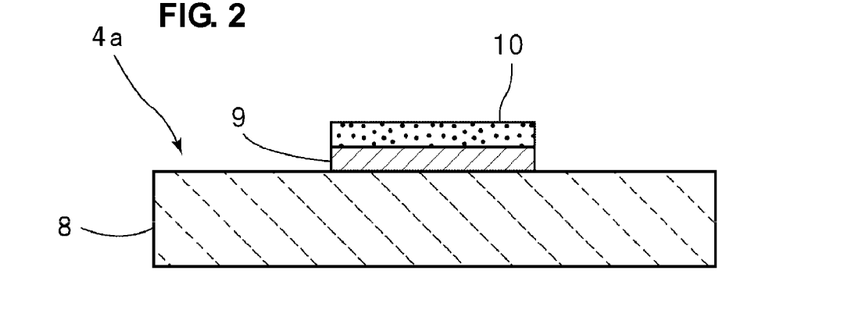
FIG. 2 is a cross-sectional view that schematically shows the structure of a sensing SAW element.
Figure 3:
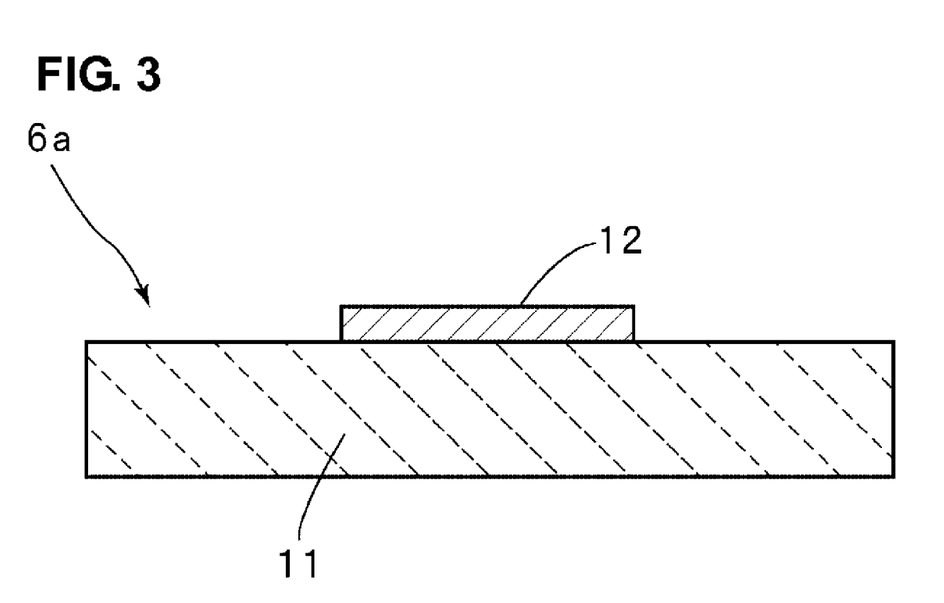
FIG. 3 is a cross-sectional view that schematically shows the structure of a reference SAW element.

The sensing SAW element 4a and the reference SAW element 6a are, for example, defined by SAW elements in which an IDT is provided on a piezoelectric substrate. As schematically shown in FIG. 2, in the sensing SAW element 4a, an IDT 9 is provided on the upper surface of a piezoelectric substrate 8, and a reaction film 10 is arranged so as to cover the IDT 9. In addition, in the reference SAW element 6a, as schematically shown in FIG. 3, an IDT 12 is provided on a piezoelectric substrate 11. The reference SAW element 6a does not include a reaction film 10.

As the sensing SAW element 4a is brought into contact with a liquid including a detection target substance, the reaction film 10 reacts with the detection target substance and, for example, the detection target substance, such as a protein, bonds with the reaction film 10. As a result, a mass applied to the IDT 9 is varied. This variation in mass changes an output frequency of the oscillator circuit 2a, and based on the frequency variation, the presence or absence of a detection target substance and the concentration thereof are measured.

In addition, in order to remove noise, or the like, due to a variation in temperature, the reference oscillator circuit 3a that uses the reference SAW element 6a is also formed. That is, by subtracting the result obtained by the reference oscillator circuit from the result obtained by the sensing oscillator circuit, background noise or noise due to a variation in temperature is removed to thereby make it possible to accurately measure the presence or absence of a detection target substance and the thickness thereof.

Moreover, m (m is an integer greater than or equal to 2) sensing oscillator circuits 2a to 2m and n (n is an integer greater than or equal to 2) reference oscillator circuits 3a to 3n are provided in the sensor for detecting a substance in a liquid 1 of the present preferred embodiment. Thus, as will be apparent from a method for detecting a substance in a liquid that uses the sensor for detecting a substance in a liquid of the present preferred embodiment, which will be described later, it is possible to highly accurately detect the presence or absence of a substance in a liquid and the concentration thereof with high sensitivity.

An oscillator circuit device 13 that includes the m sensing oscillator circuits 2a to 2m and the n reference oscillator circuits 3a to 3n is connected to a controller 14 so as to enter an on state based on a signal from the controller 14 to initiate operation.

A frequency counter 15 is connected to the oscillator circuit device 13. The frequency counter 15 is switched so as to be connected to any one of the m sensing oscillator circuits 2a to 2m and n reference oscillator circuits 3a to 3n, and counts the output frequency of the corresponding sensing oscillator circuit 2a to 2n or reference oscillator circuit 3a to 3n to output the counted frequency. A recording unit 16 is connected to the downstream side of the frequency counter 15. The recording unit 16 records a frequency signal supplied from the frequency counter 15.

The controller 14 is connected to the frequency counter 15 and the recording unit 16. The controller 14 drives the frequency counter 15, sequentially connects the frequency counter 15 to the sensing oscillator circuits 2a to 2m and then sequentially connects the frequency counter 15 to the reference oscillator circuit 3a to 3n to thereby cause the recording unit 16 to record the output frequencies thereof.

In addition, the controller 14 determines whether the frequency drift of each of the output frequencies of the sensing oscillator circuits 2a to 2m and each of the output frequencies of the n reference oscillator circuits 3a to 3n, which are recorded in the recording unit 16, falls within a set range, selects the sensing oscillator circuits and the reference oscillator circuits which are determined to fall within the set range and are allowed, and then detects the presence or absence of a substance in a liquid and the concentration thereof based on outputs of the selected sensing oscillator circuits and reference oscillator circuits.

A specific preferred embodiment of a method for detecting substance in a liquid that uses the sensor for detecting a substance in a liquid 1 will be described with reference to FIG. 4.

Figure 4:
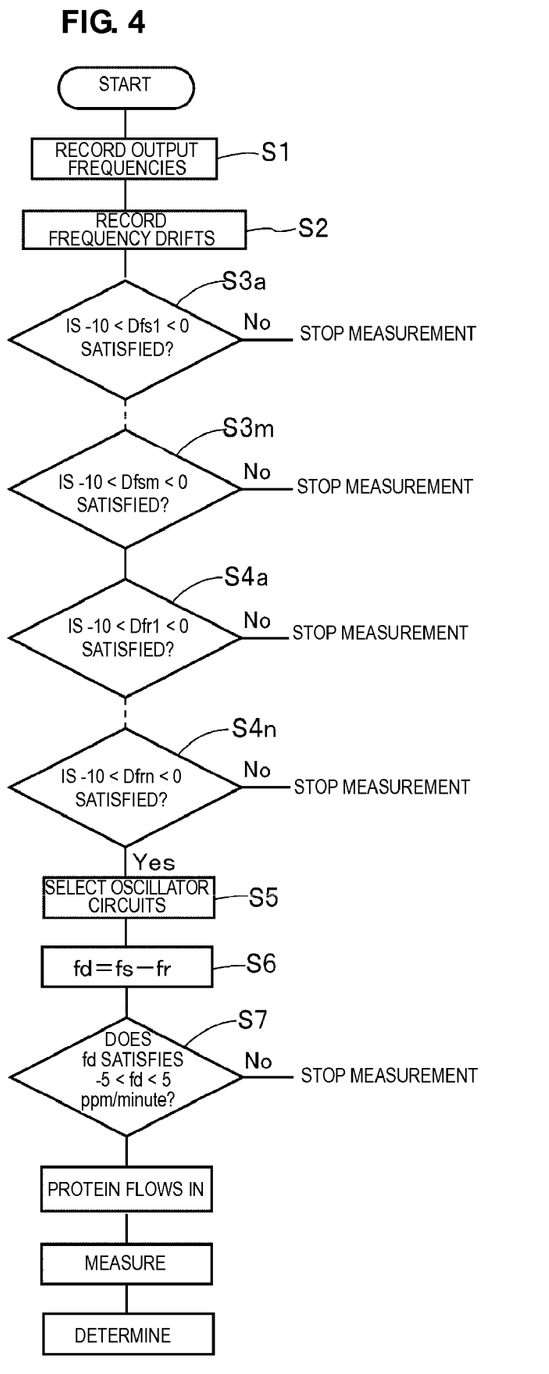
FIG. 4 is a flowchart of a method for detecting a substance in a liquid according to a preferred embodiment of the present invention.

FIG. 4 is flowchart of the method for detecting a substance in a liquid according to the present preferred embodiment. First, the sensing SAW elements 4a to 4m of the sensing oscillator circuits 2a to 2m and the reference SAW elements 6a to 6n of the reference oscillator circuits 3a to 3n in the sensor for detecting a substance in a liquid 1 are brought into contact with a liquid. In step S1, they are brought into contact with a liquid that does not include a detection target substance. In this state, the controller 14 drives the oscillator circuit device 13 to initiate measurement (step S1). In step S1, the frequency counter 15 is sequentially connected to the m sensing oscillator circuits 2a to 2m and then sequentially connected to the reference oscillator circuits 3a to 3n, and the output signals of these oscillator circuits 2a to 2m, 3a to 3n are sequentially recorded in the recording unit 16.

Next, in step S2, the frequency drifts Dfs1 to Dfsm of the output frequencies fs1 to fsm of the sensing oscillator circuits 2a to 2m and the frequency drifts Dfr1 to Dfrn of the output frequencies fr1 to frn of the outputs of the reference oscillator circuits are measured and recorded in the recording unit 16.

After that, in steps S3a to S3m, it is respectively determined whether the frequency drifts Dfs1 to Dfsm of the sensing oscillator circuits 2a to 2m are in the range of about −10 ppm to about 0, that is, within a predetermined range. In steps S3a to S3m, when the frequency drift Dfs1 to Dfsm of the output frequency of the sensing oscillator circuit 2a to 2m falls outside the predetermined range, measurement using the sensing oscillator circuit that falls outside the predetermined range is stopped.

Thus, in steps S3a to S3m, the sensing oscillator circuits, of which the frequency drifts fall within the predetermined range, that is, the frequency drifts that are determined to be acceptable, are selected, and measurements only by the selected sensing oscillator circuits are continued.

Next, in steps S4a to S4n, it is respectively determined whether the frequency drifts Dfr1 to Dfrn of the output frequencies fall within a predetermined range. The above predetermined range is substantially equal to the predetermined range by which the frequency drifts of the sensing oscillator circuits 2a to 2m are determined. That is, preferably, the range of about −10 ppm/minute to about 0 ppm/minute, for example, is selected as the predetermined range in the present preferred embodiment.

Thus, in step S4a to step S4n, among the reference oscillator circuits 3a to 3n, when the frequency drift falls outside the predetermined range, measurement using the reference oscillator circuit that falls outside the predetermined range is stopped. On the other hand, measurements are continued using the reference oscillator circuits whose frequency drifts fall within the predetermined range and are determined to be acceptable.

The steps 3a to 3m and steps 4a to 4n correspond to a third step according to this preferred embodiment of the present invention.

Next, in step S5, at least one of the sensing oscillator circuits that has a characteristic close to a desired characteristic and at least one of the reference oscillator circuits that has a characteristic close to a desired characteristic are selected from among the acceptable sensing oscillator circuits and acceptable reference oscillator circuits. Here, the desired characteristic is a target characteristic stored in the controller in advance. That is, at least one of the sensing oscillator circuits close to the target characteristic, and at least one of the reference oscillator circuits close to the target characteristic are selected in step S5. In this case, the desired characteristic is not limited to the target characteristic stored in the controller 14 in advance. Instead, the desired characteristic may be such that, from among the acceptable sensing oscillator circuits and the acceptable reference oscillator circuits, at least one of the sensing oscillator circuits of which the frequency drifts have a similar characteristic and at least one of the reference oscillator circuits of which the frequency drifts have a similar characteristic are respectively selected. That is, the desired characteristics may be approximate values of the frequency drifts of the sensing oscillator circuit and reference oscillator circuit whose frequency drifts are close to one another. The step S5 corresponds to a fourth step.

Next, in step S6, a liquid that includes a detection target substance is brought into contact with the sensor for detecting a substance in a liquid 1, an oscillator circuit output of the at least one of the sensing oscillator circuits selected in step S5 and an oscillator circuit output of the at least one of the reference oscillator circuits selected in step S5 are compared in the controller 14, and thereby the detection target substance is detected. The step S6 corresponds to a fifth step.

Figure 5:
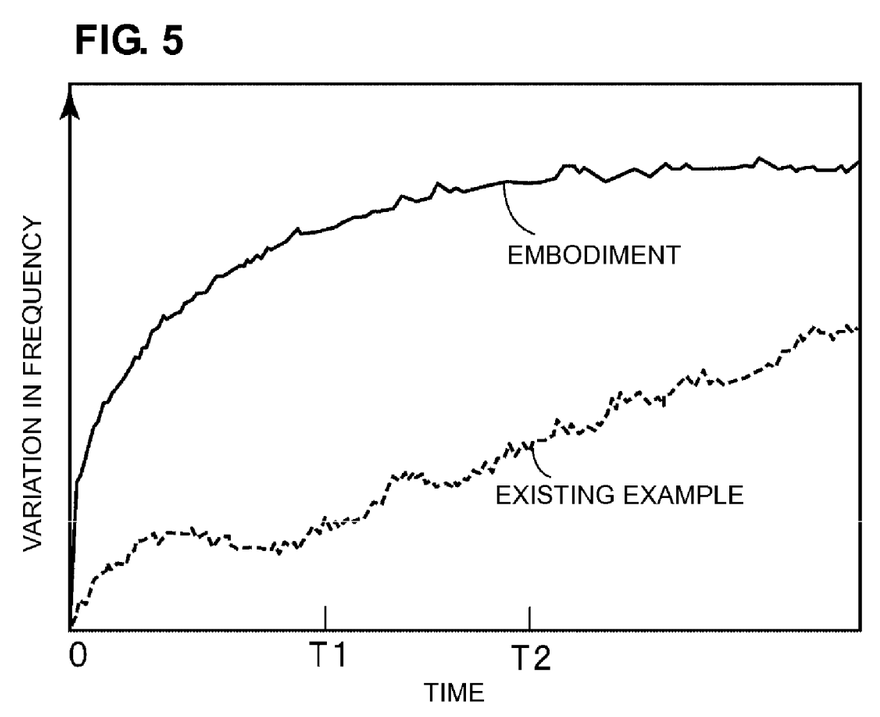
FIG. 5 is graph that shows a variation in normalized frequency corresponding to a concentration of a detection target substance in each of the method for detecting substance in a liquid according to a preferred embodiment of the present invention and a known method for detecting substance in a liquid.

The result of the detection when PHOSPHATE BUFFERED SALINE (PBS) that includes a Protein A is used as a sample is shown by the solid line in FIG. 5. Note that the abscissa axis of FIG. 5 represents time, and the ordinate axis of FIG. 5 represents a variation in the frequency corresponding to the concentration of the Protein A. More specifically, when a difference between the oscillatory frequency of the sensing oscillator circuit and the oscillatory frequency fr of the reference oscillator circuit is $\Delta f$, a variation in frequency after t hours has elapsed is expressed by $\Delta f(t)/fr(t)$, and a variation in frequency of the ordinate axis of FIG. 5 means $\Delta f(t)/fr(t)$. In addition, FIG. 5 shows the result of a known method for detecting a substance in a liquid. In the known example, the result is shown by measuring the same sample using only one sensing oscillator circuit and only one reference oscillator circuit.

In the known example shown by the broken line, the sensitivity is relatively low until around time T1 but the variation in frequency is substantially constant. However, after time T1, the variation in frequency increases over time. Therefore, it is difficult to maintain the variation in frequency that corresponds to the concentration of a protein constant. In contrast, in the present preferred embodiment, as time elapses from time T1 to time T2, the variation in frequency is gradually saturated. Therefore, the variation in frequency that corresponds to the concentration of a protein can be stably and accurately measured. In addition, with the saturation of the variation in frequency, the variation in frequency is increased, and therefore, a protein can be detected with extremely high sensitivity.

This is because, in the present preferred embodiment, as described above, from among the m sensing oscillator circuits 2a to 2m and the n reference oscillator circuits 3a to 3n, a relatively stable sensing oscillator circuit and a relatively stable reference oscillator circuit that are determined to be acceptable in the above described method, that is, whose frequency drifts are relatively small, are selected and then measurement is performed.

Thus, according to the present preferred embodiment, even when the characteristics of the m sensing SAW elements 4a to 4m defining the sensing oscillator circuits 2a to 2m and the reference SAW elements 6a to 6n defining the reference oscillator circuits 3a to 3n are dispersed, it is possible to accurately detect the presence or absence of a detection target substance and the concentration thereof with high sensitivity.

In addition, in the present preferred embodiment, as described above, measurements using the sensing oscillator circuits and reference oscillator circuits whose frequency drifts are determined to fall outside the predetermined range are stopped and are rejected in steps S3a to S3m and steps S4a to S4n. Because, after the steps S3a to S3m and steps S4a to S4n, measurements using the rejected sensing oscillator circuits or the rejected reference oscillator circuits are stopped, it is possible to reduce the time required for the following process. That is, it is possible to reduce the time required to switch the frequency counter 15 to conduct the following measurements.

In addition, in the present preferred embodiment, the predetermined range for determining whether the frequency drift of the oscillator circuit output of each of the sensing oscillator circuits 2a to 2m and reference oscillator circuits 3a to 3n is acceptable or unacceptable preferably uses the range of about −10 ppm/minute to about 0 ppm/minute, for example. Instead, the predetermined range may be appropriately changed in accordance with the desired sensitivity and accuracy of the sensor for detecting a substance in a liquid.

That is, by narrowing the predetermined range, it is possible to more accurately detect a detection target substance.

In the controller 14, using an oscillator circuit output from the at least one of the sensing oscillator circuits, which is determined to be acceptable, and an oscillator circuit output from the at least one of the reference oscillator circuits, which is determined to be acceptable, the presence or absence of a detection target substance and the concentration thereof are measured. In this case, when the plurality of sensing oscillator circuits are determined to be acceptable, it is preferable to use the average of the plurality of outputs of the sensing oscillator circuits. Similarly, for the reference oscillator circuit output, when the plurality of reference oscillator circuits are determined to be acceptable, it is preferable to use the average of the plurality of outputs of the reference oscillator circuits that are determined to be acceptable. Using the average of the plurality of outputs of the sensing oscillator circuits and/or the plurality of outputs of the reference oscillator circuits, it is possible to further increase the accuracy of measurement.

In step S5 of the preferred embodiment described above, when at least one of the sensing oscillator circuits and at least one of the reference oscillator circuits are selected for the "desired characteristic" as a selection criterion, a characteristic having a minimum frequency drift is preferably selected. In this case, by selecting one sensing oscillator circuit having a minimum frequency drift and one reference oscillator circuit having a minimum frequency drift, it is possible to reliably prevent a decrease in measurement accuracy due to a frequency drift.

After at least one sensing oscillator circuit and at least one reference oscillator circuit are selected in step S5, in step S6, a frequency difference fd=fs−fr between the output frequency fs of the selected sensing oscillator circuit and the output frequency fr of the selected reference oscillator circuit is calculated by the controller 14. In this case, when the plurality of sensing oscillator circuits are selected, the output frequency fs of the sensing oscillator circuit may preferably use the average of the output frequencies fs of the plurality of selected sensing oscillator circuits. Similarly, when the plurality of reference oscillator circuits are selected, the average of the output frequencies of the plurality of reference oscillator circuits may preferably be used for the output frequency fr of the reference oscillator circuit.

Then, subsequent to step S6, in step S7, it is determined whether the frequency difference fd calculated in step S6 falls within a predetermined range. The predetermined range is a frequency difference between the output frequency fs of the sensing oscillator circuit and the output frequency fr of the reference oscillator circuit and is appropriately selected in accordance with the desired measurement accuracy.

In the present preferred embodiment, it is determined in step S7 whether the frequency difference fd falls within a range of about −5 (ppm/minute)/fd<about +5 (ppm/minute). Then, in S7, when the frequency difference fd falls within the predetermined range, the sensing sensitivity is sufficient, whereas when it falls outside the predetermined range, sensing sensitivity is poor, and thus, not sufficient. In this manner, when the sensing sensitivity is sufficient, in step S8, a detection target substance is detected. Note that when the frequency difference fd falls outside the predetermined range and it is determined that the sensing sensitivity is not sufficient, the process returns to step S1 and the measurement will be performed again.

In the present preferred embodiment, steps S6 and S7 determine, based on the frequency difference fd, whether the sensing sensitivity is sufficient or insufficient. Thus, a frequency difference between the sensing oscillator circuit and the reference oscillator circuit is reliably reduced and, as a result, it is possible to further enhance measurement sensitivity.

However, in preferred embodiments of the present invention, the steps S6 and S7 are not always necessary. That is, it is also applicable that without performing the steps S6 and S7, detection is initiated in accordance with the step S8 from the above described step S5.

In addition, in the step S7, the predetermined range that is used when it is determined whether the frequency difference fd is within the predetermined range is not limited to the range in which the absolute value of the frequency difference fd is less than about 5 ppm/minute. The predetermined range may be appropriately selected in accordance with the desired sensing sensitivity. Of course, by reducing the absolute value of the frequency difference fd to be less than about 5 ppm/minute, it is possible to effectively increase the measurement sensitivity as described above.

Note that the material used for the SAW elements of the sensor for detecting a substance in a liquid used in the present preferred embodiment is not specifically limited. That is, the piezoelectric substrate may be made of a piezoelectric monocrystal, such as $LiTaO_3$, $LiNbO_3$, or rock crystal, or piezoelectric ceramics, such as PZT, for example. Furthermore, the IDT may be made of any appropriate metal, such as Al, Ag or Au or alloys thereof, for example.

The reaction film includes an appropriate immobilized material or an appropriate material, which react with a detection target substance, for example. In addition, the reaction film itself may be made of a substance that reacts with a detection target substance to bond with the detection target substance.

The detection target substance may not only be a biochemical substance, such as an antigen, an antibody, or various proteins, for example, but also may be an inorganic compound. When an antigen or an antibody is measured, it is only necessary that an antibody or an antigen that bonds with an antigen or an antibody is immobilized in the reaction film.

While preferred embodiments of the present invention have been described above, it is to be understood that variations and modifications will be apparent to those skilled in the art without departing the scope and spirit of the present invention. The scope of the present invention, therefore, is to be determined solely by the following claims.

What is claimed is:

1. A method for detecting substance in a liquid that uses a sensor for detecting a substance in a liquid that includes a sensing oscillator circuit including a sensing surface acoustic wave element with a sensing portion having an interdigital transducer and a reaction film arranged so as to cover the interdigital transducer and to react with a substance in a liquid, and a first amplifier element connected to the sensing surface acoustic wave element, a reference oscillator circuit including a reference surface acoustic wave element having an interdigital transducer but no reaction film that covers the interdigital transducer, and a second amplifier element connected to the reference surface acoustic wave element, and a recording unit that records an oscillator circuit output of the sensing oscillator circuit and an oscillator circuit output of the reference oscillator circuit, the method comprising:

providing a number m of the sensing oscillator circuits, where m is an integer greater than or equal to 2, and a number n of the reference oscillator circuits, where n is an integer greater than or equal to 2;

a first step of recording output frequencies of the m sensing oscillator circuits and output frequencies of the n reference oscillator circuits;

a second step of measuring a frequency drift of each of the output frequencies of the m sensing oscillator circuits and each of the output frequencies of the n reference oscillator circuits;

a third step of determining that, when the frequency drift measured in the second step falls within a predetermined range, the corresponding sensing oscillator circuit or the corresponding reference oscillator circuit is acceptable and, when the frequency drift falls outside the predetermined range, the corresponding sensing oscillator circuit or the corresponding reference oscillator circuit is unacceptable;

a fourth step of selecting at least one of the sensing oscillator circuits having a frequency drift that is approximately the same as a desired frequency drift from among the sensing oscillator circuits determined to be acceptable in the third step and at least one of the reference oscillator circuits having a frequency drift that is approximately the same as a desired frequency drift from among the reference oscillator circuits determined to be acceptable in the third step; and a fifth step of bringing a liquid that includes a detection target substance into contact with the sensor for detecting a substance in the liquid and comparing an output frequency of the at least one of the sensing oscillator circuits selected the fourth step with an output frequency of the at least one of the reference oscillator circuits selected in the fourth step to thereby detect the detection target substance.

2. The method for detecting substance in liquid according to claim 1, wherein the unacceptable sensing oscillator circuits and the unacceptable reference oscillator circuits are not used in the following steps after they are determined to be unacceptable in the third step.

3. The method for detecting substance in liquid according to claim 1, wherein in the third step, the predetermined range of the frequency drift is about −10 ppm/minute to about 0 ppm/minute.

4. The method for detecting substance in liquid according to claim 3, wherein in the third step, at least one of the sensing oscillator circuits is selected in order from the sensing oscillator circuit having a smaller frequency drift and at least one of the reference oscillator circuits is selected in order from the reference oscillator circuit having a smaller frequency drift.

5. The method for detecting substance in liquid according to claim 1, wherein in the fifth step, the detection target substance is detected using an average of the output frequencies of the reference oscillator circuits, an average of the output frequencies of the sensing oscillator circuits, and variations in outputs of the sensing oscillator circuits due to the detection target substance.

6. The method for detecting substance in liquid according to claim 1, wherein in the third step and the fourth step, one sensing oscillator circuit having a minimum frequency drift is selected from among the m sensing oscillator circuits and one reference oscillator circuit having a minimum frequency drift is selected from among the n reference oscillator circuits.

7. The method for detecting substance in liquid according to claim 1, further comprising:

between the fourth step and the fifth step, a sixth step of, where an output frequency of the selected at least one of the sensing oscillator circuits is a sensing frequency $f_s$ and an output frequency of the selected at least one of the reference oscillator circuits is a reference frequency $f_r$, calculating a frequency difference $f_d = f_s − f_r$; and a seventh step of determining that, when the frequency difference fd falls within a predetermined range, sensing sensitivity is sufficient and, when the frequency difference fd falls outside the predetermined range, sensing sensitivity is insufficient.

8. The in-liquid substance detection unit according to claim 7, wherein in the seventh step, the predetermined range of the frequency difference fd is about −5 ppm/minute<fd<about 5 ppm/minute.

* * * * *